United States Patent
Kawarada

(10) Patent No.: US 7,339,212 B2
(45) Date of Patent: Mar. 4, 2008

(54) P CHANNEL FILED EFFECT TRANSISTOR AND SENSOR USING THE SAME

(75) Inventor: Hiroshi Kawarada, Yokohama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 31 days.

(21) Appl. No.: 10/549,764

(22) PCT Filed: Mar. 25, 2004

(86) PCT No.: PCT/JP2004/004196

§ 371 (c)(1),
(2), (4) Date: Jul. 10, 2006

(87) PCT Pub. No.: WO2004/086025

PCT Pub. Date: Oct. 7, 2004

(65) Prior Publication Data

US 2006/0254910 A1   Nov. 16, 2006

(30) Foreign Application Priority Data

Mar. 25, 2003   (JP) ............................. 2003-082986

(51) Int. Cl.
*H01L 23/58*   (2006.01)
*H01L 24/00*   (2006.01)
(52) U.S. Cl. ................ 257/253; 257/414; 257/E29.299
(58) Field of Classification Search ................ 257/414, 257/253, E29.299
See application file for complete search history.

(56) References Cited

U.S. PATENT DOCUMENTS 4,968,400 A * 11/1990 Shimomura et al. ........ 257/253

FOREIGN PATENT DOCUMENTS

| JP | 8-240555 | 9/1996 |
|----|----------|--------|
| JP | 2001-272372 | 10/2001 |
| JP | 2002-286692 | 10/2002 |
| JP | 2004-109020 | 4/2004 |

* cited by examiner

*Primary Examiner*—Evan Pert
(74) *Attorney, Agent, or Firm*—Oblon, Spivak, McClelland, Maier & Neustadt, P.C.

(57) ABSTRACT

A p channel field effect transistor in which the sensitivity of an enzyme can be enhanced by immobilizing the enzyme directly on an FET channel surface (diamond surface), as well as a sensor including the same, is provided. A diamond surface (22) having mixed hydrogen terminals, oxygen terminals, and amino terminals is treated under the action of glutaraldehyde $OHC(CH_2)_3CHO$ (30), so that the glutaraldehyde (30) is immobilized on the diamond surface (22) having mixed hydrogen terminals, oxygen terminals, and amino terminals. Subsequently, urease (29) is further applied thereto, so that the amino group (31) of the urease (29) is bonded to the glutaraldehyde (30). That is, the urease (29) can be immobilized on the diamond surface (22) having mixed hydrogen terminals, oxygen terminals, and amino terminals. When the urea concentration is increased from $10^{-6}$ M to $10^{-2}$ M, the threshold voltage shifts by about 0.1 V in the positive direction, and the sensitivity to urea concentration of 30 mV/decade is exhibited.

9 Claims, 10 Drawing Sheets

(a)

(b)

(c)

P CHANNEL FILED EFFECT TRANSISTOR AND SENSOR USING THE SAME

TECHNICAL FIELD

The present invention relates to a p channel field effect transistor and a sensor including the same. In particular, it relates to a chemical sensor and a biosensor.

BACKGROUND ART

The inventor of the present invention has proposed a field effect transistor in which a liquid electrolyte has been used as a gate, and a hydrogen terminated surface of a diamond has served as a channel (refer to the following Patent Documents 1 and 2).

It is known that urea is hydrolyzed by the catalysis of urease (enzyme), ammonia is generated, and the pH is increased. In a silicon based ion-sensitive field effect transistor (ISFET), urease (enzyme) is immobilized on a silicon nitride serving as a protective-sensitive film and, thereby, a change in pH is detected. In this case, the detection accuracy depends on the immobilization density and the immobilization strength. Although there is a method in which urease (enzyme) and the ISFET are separated, in this case, a problem occurs in that the detection sensitivity is reduced.

[Patent Document 1]
Japanese Patent No. 3313696 (pages 2 to 4, FIG. 1)
[Patent Document 2]
Japanese Patent No. 3390756 (pages 2 to 4, FIG. 1)

DISCLOSURE OF INVENTION

In consideration of the above-described circumstances, it is an object of the present invention to provide a p channel field effect transistor in which the sensitivity of an enzyme can be enhanced by immobilizing the enzyme directly on an FET channel surface (diamond surface), as well as a sensor including the same.

In particular, it is an object of the present invention to provide a p channel field effect transistor in which the sensitivity to urea concentration can be enhanced by immobilizing urease directly on an FET channel surface (diamond surface), as well as a sensor including the same.

The present invention was made in order to achieve the above-described object.

[1] In a p channel field effect transistor, a liquid electrolyte is used as a gate, and a polycrystalline or monocrystalline diamond surface having mixed hydrogen terminals, oxygen terminals and amino terminals serves as a channel.

[2] A sensor is characterized by including the p channel field effect transistor described in the above item [1] and exhibiting a pH sensitivity through the use of a shift of threshold voltage in the positive direction on the above-described surface having mixed amino terminals and oxygen terminals in response to an increase in pH of the above-described liquid electrolyte.

[3] The sensor described in the above item [2] is characterized in that the above-described increase in pH is 2 to 12.

[4] The sensor described in the above item [2] or [3] is characterized in that urease is immobilized to the amino terminal on the above-described surface with glutaraldehyde (divalent aldehyde) therebetween, the threshold voltage shifts in the positive direction in response to an increase in urea concentration and, thereby, the sensitivity to urea is exhibited.

[5] The sensor described in the above item [4] is characterized in that the above-described increase in urea concentration is $10^{-6}$ M to $10^{-2}$ M.

BEST MODE FOR CARRYING OUT THE INVENTION

The embodiments of the present invention will be described below in detail.

Figure 1:
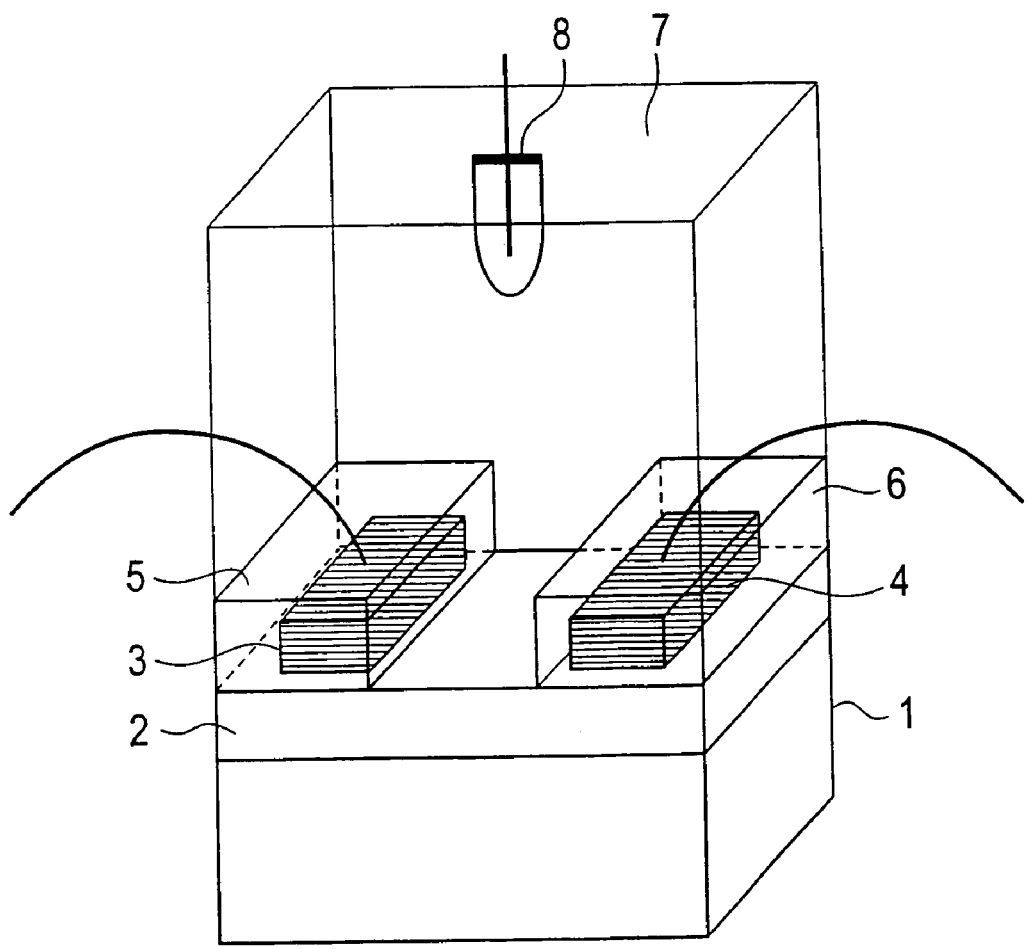
FIG. 1 is a perspective view of a diamond FET with an electrolytic solution gate, according to the present invention.
Figure 2:
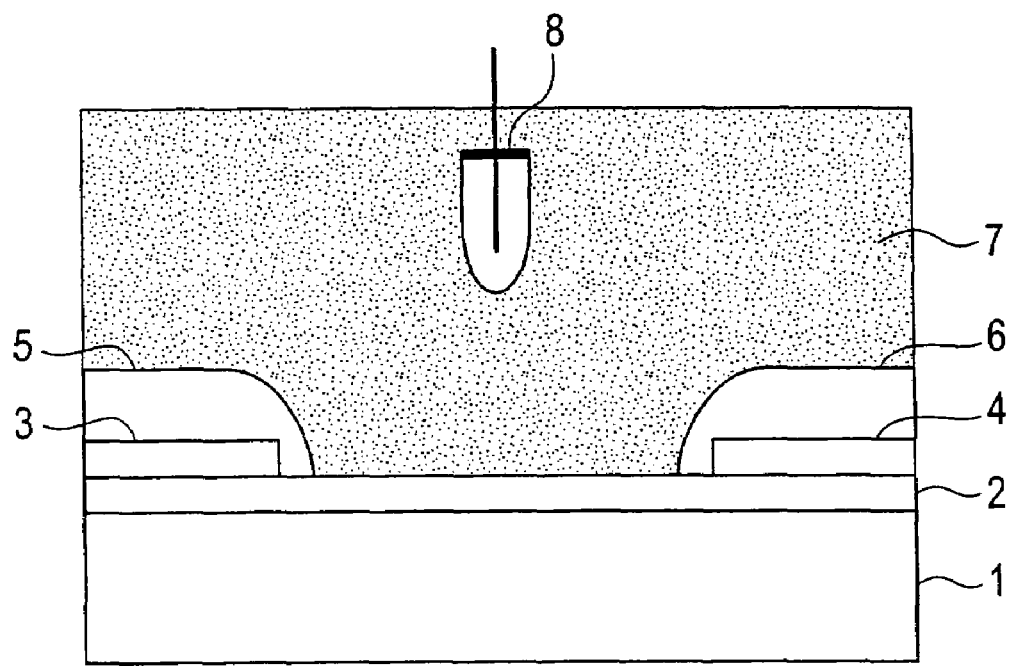
FIG. 2 is a sectional view of a diamond FET with an electrolytic solution gate, according to an embodiment of the present invention.

FIG. 1 is a perspective view of a diamond FET with an electrolytic solution gate, according to the present invention. FIG. 2 is a sectional view of the diamond FET with an electrolytic solution gate.

In these drawings, reference numeral 1 denotes a polycrystalline CVD diamond substrate, reference numeral 2 denotes a P-type surface conductive layer, reference numeral 3 denotes a source electrode (Au), reference numeral 4 denotes a drain electrode (Au), reference numeral 5 denotes an epoxy resin covering the source electrode (Au) 3, reference numeral 6 denotes an epoxy resin covering the drain electrode (Au) 4, reference numeral 7 denotes an electrolytic solution, and reference numeral 8 denotes a gate electrode (Ag/AgCl reference electrode).

This diamond biosensor with an electrolytic solution gate includes the inexpensive polycrystalline CVD diamond substrate and, therefore, cost reduction can be achieved as compared with a known silicon biosensor having a source-drain on a silicon substrate.

In the silicon biosensor, signals are detected through silicon nitride and silicon dioxide. However, in the diamond sensor including no protective film nor sensitive film, signals can be directly detected. Consequently, the diamond sensor can detect signals with no noise.

In the present invention, a hydrogen-terminated diamond surface is modified by using an ultraviolet ray.

That is, when oxygen is introduced and the ultraviolet ray is applied, the hydrogen-terminated surface is partially oxidized by ozone and, thereby, is oxygen-terminated. When a substrate is put into an ammonia solution and is irradiated with the ultraviolet ray, the hydrogen-terminated diamond surface is partially amino-terminated. Since the oxygen-terminal and the amino-terminal have an insulating property, the conductance of the FET with an electrolytic solution gate is decreased to some extent, but an influence exerted on the device action is small.

Figure 3:
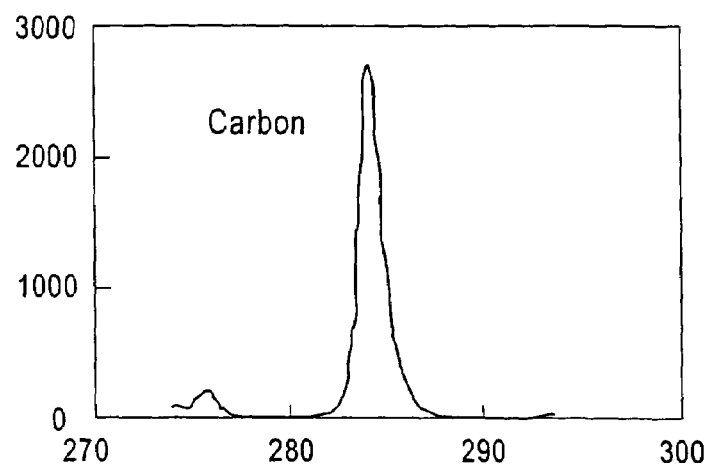
FIG. 3 is a diagram showing the XPS measurement results of an aminated substrate according to the present invention.
Figure 3:
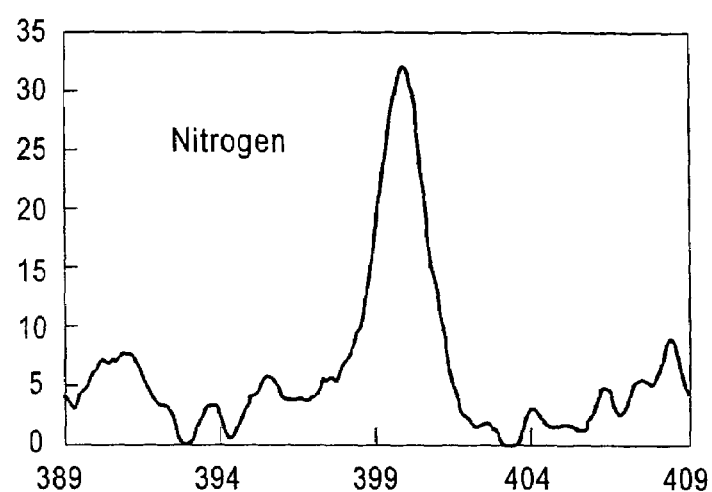
Figure 3:
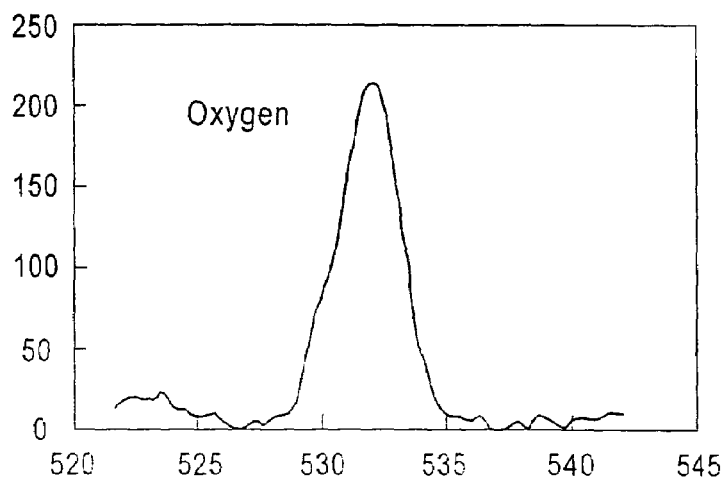

FIG. 3 is a diagram showing the XPS measurement results of an aminated substrate according to the present invention.

These are the XPS measurement results of the amino-terminated substrate, where the substrate was put into an ammonia solution and was irradiated with an ultraviolet ray. FIG. 3(a) relates to carbon, FIG. 3(b) relates to nitrogen, and FIG. 3(c) relates to oxygen. In these drawings, a peak of nitrogen and a peak of oxygen are observed. As is clear from this, when the ultraviolet ray is applied to the substrate in the ammonia solution, a hydrogen-terminated surface is partially amino-terminated and oxygen-terminated. In these drawings, the vertical axis indicates a photoelectron detection intensity (arbitrary unit), and the horizontal axis indicates a bond energy.

Figure 4:
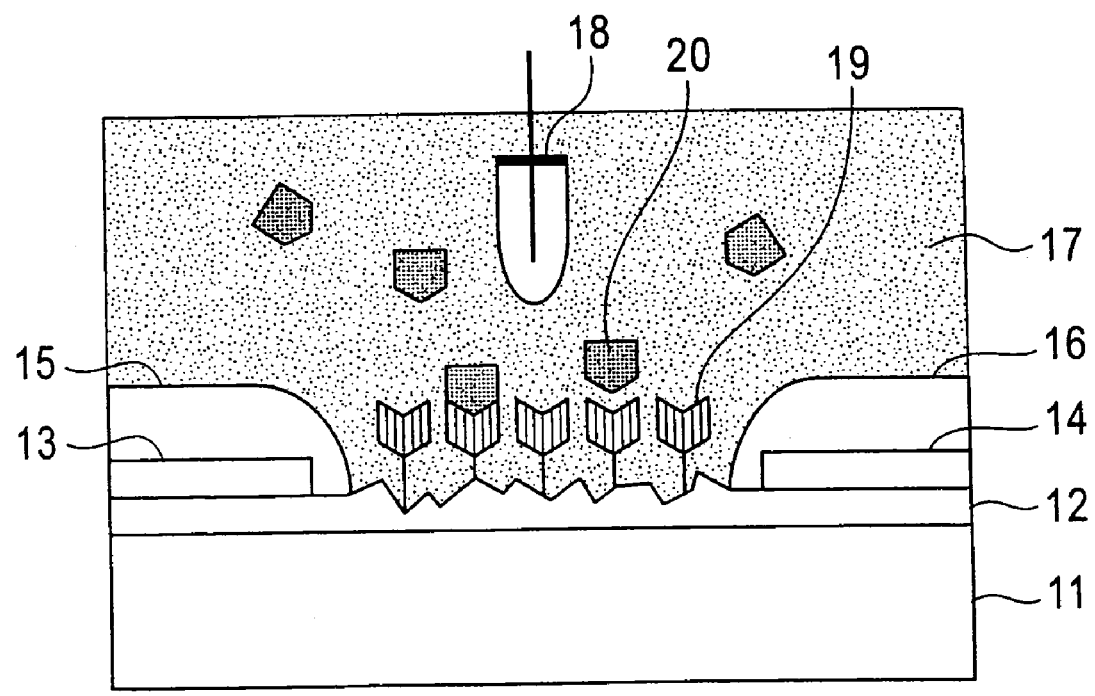
FIG. 4 is a schematic diagram of an enzyme biosensor with an electrolytic solution gate, according to an embodiment of the present invention.

FIG. 4 is a schematic diagram of an enzyme biosensor with an electrolytic solution gate, according to an embodiment of the present invention.

In this drawing, reference numeral 11 denotes a polycrystalline CVD diamond substrate, reference numeral 12 denotes a P-type surface conductive layer (hydrogen-, oxygen-, and amino-terminated substrate surface), reference numeral 13 denotes a source electrode (Au), reference numeral 14 denotes a drain electrode (Au), reference numeral 15 denotes an epoxy resin covering the source electrode (Au) 13, reference numeral 16 denotes an epoxy resin covering the drain electrode (Au) 14, reference numeral 17 denotes an electrolytic solution, reference numeral 18 denotes a gate electrode (Ag/AgCl reference electrode), reference numeral 19 denotes an enzyme, and reference numeral 20 denotes a substrate.

An FET with an electrolytic solution gate was produced on a surface channel of the hydrogen-, oxygen-, and amino-terminated polycrystalline diamond substrate 11.

As shown in FIG. 4, the enzymes 19 can be immobilized directly on the P-type surface conductive layer (substrate surface in which a part of the hydrogen-terminated surface is amino-terminated and oxygen-terminated) 12, the substrates 20 in the electrolytic solution 17 can be bonded to these enzymes 19.

Figure 5:
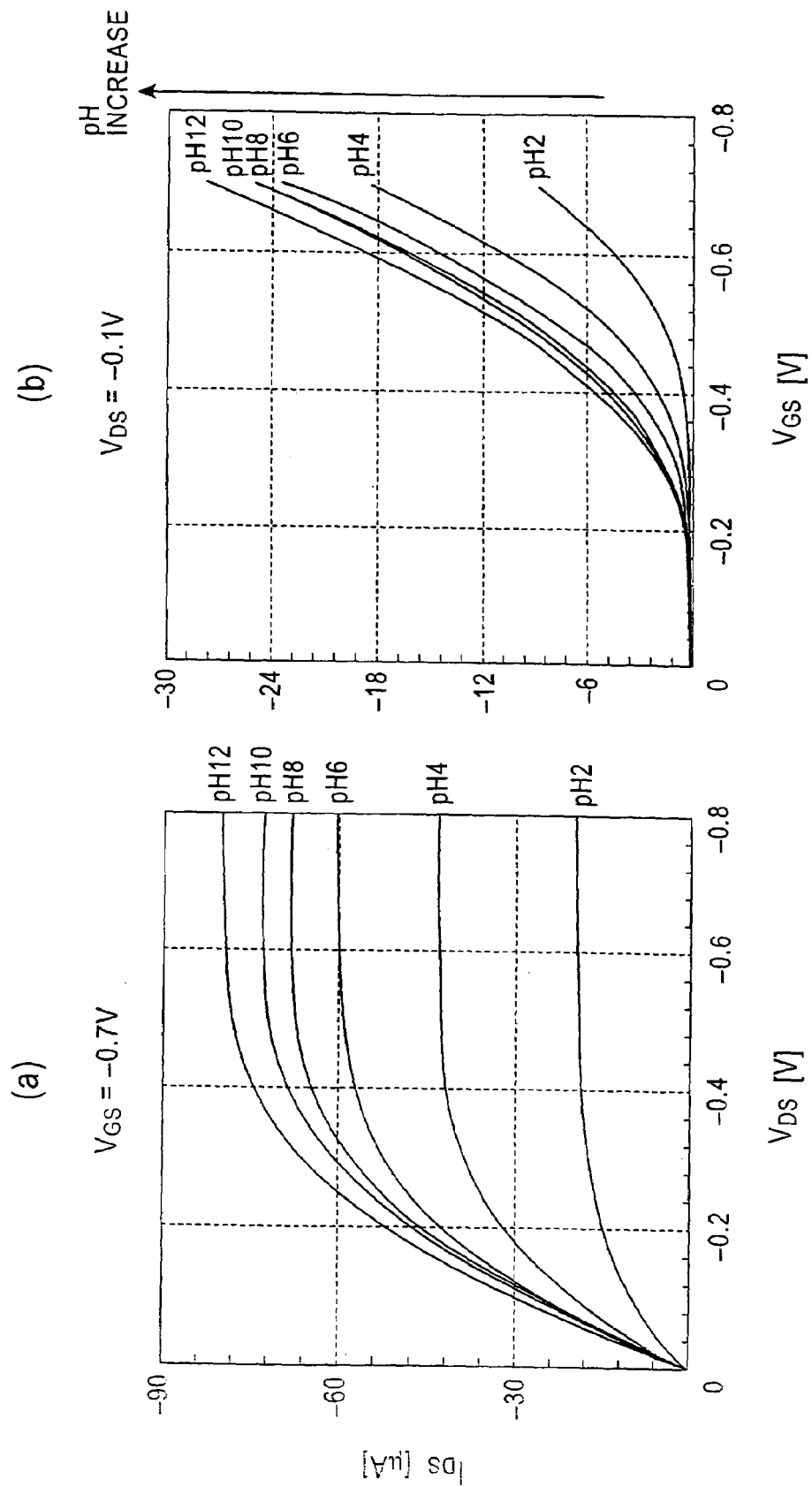
FIG. 5 is a diagram (No. 1) showing the pH sensitivity of a hydrogen-terminated diamond substrate which is partially amino-terminated and oxygen-terminated.

FIG. 5 is a diagram (No. 1) showing the pH sensitivity of a hydrogen-terminated diamond substrate which is partially amino-terminated and oxygen-terminated, according to an embodiment of the present invention. FIG. 5(a) is a characteristic diagram showing the drain-to-source voltage $V_{DS}$ versus the drain-to-source current $I_{DS}$ in the case where the gate-to-source voltage $V_{GS}$ is −0.7 V. FIG. 5(b) is a characteristic diagram showing the gate-to-source voltage $V_{GS}$ versus the drain-to-source current $I_{DS}$ in the case where the drain-to-source voltage $V_{DS}$ is −0.1 V.

In these cases, the pH sensitivity was exhibited when the pH was 2 to 12.

Figure 6:
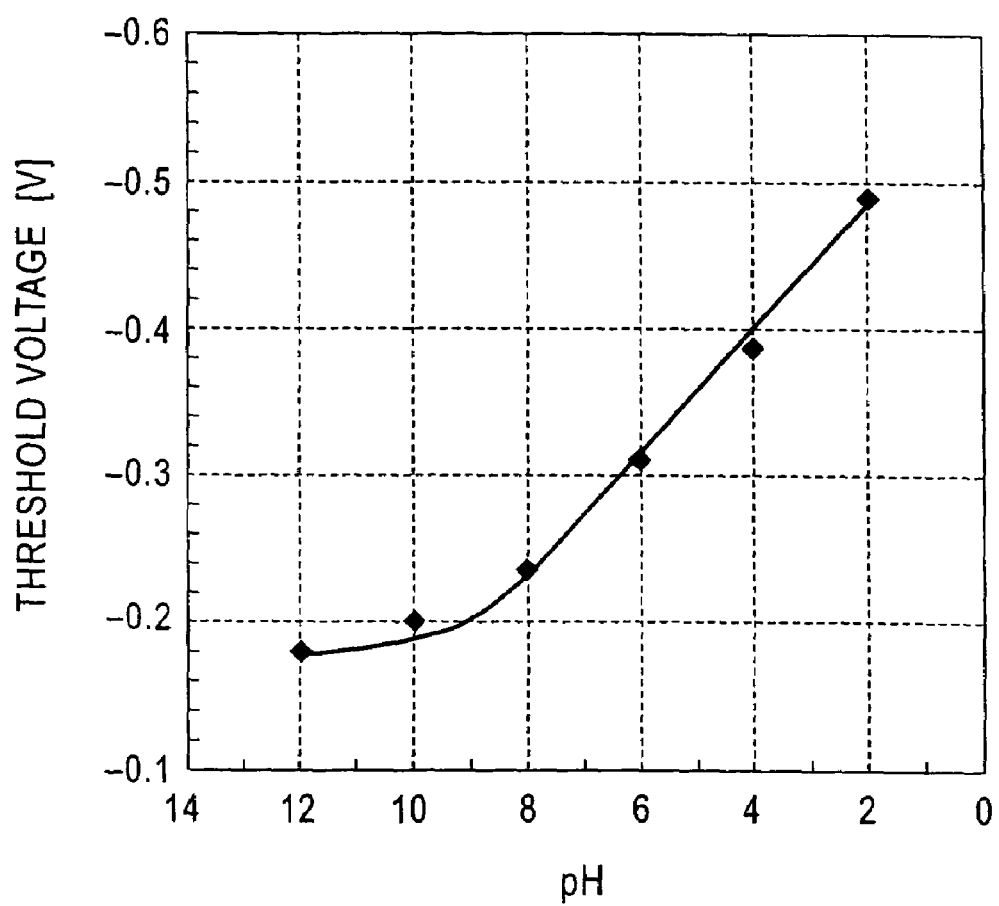
FIG. 6 is a diagram (No. 2) showing the pH sensitivity of a hydrogen-terminated diamond substrate which is partially amino-terminated and oxygen-terminated.

FIG. 6 is a diagram (No. 2) showing the pH sensitivity of a hydrogen-terminated diamond substrate which is partially amino-terminated and oxygen-terminated, according to an embodiment of the present invention. In this drawing, the horizontal axis indicates the pH, and the vertical axis indicates the threshold voltage [V].

As is clear from these drawings, the hydrogen-terminated diamond substrate which is partially amino-terminated and oxygen-terminated has the pH sensitivity.

Figure 7:
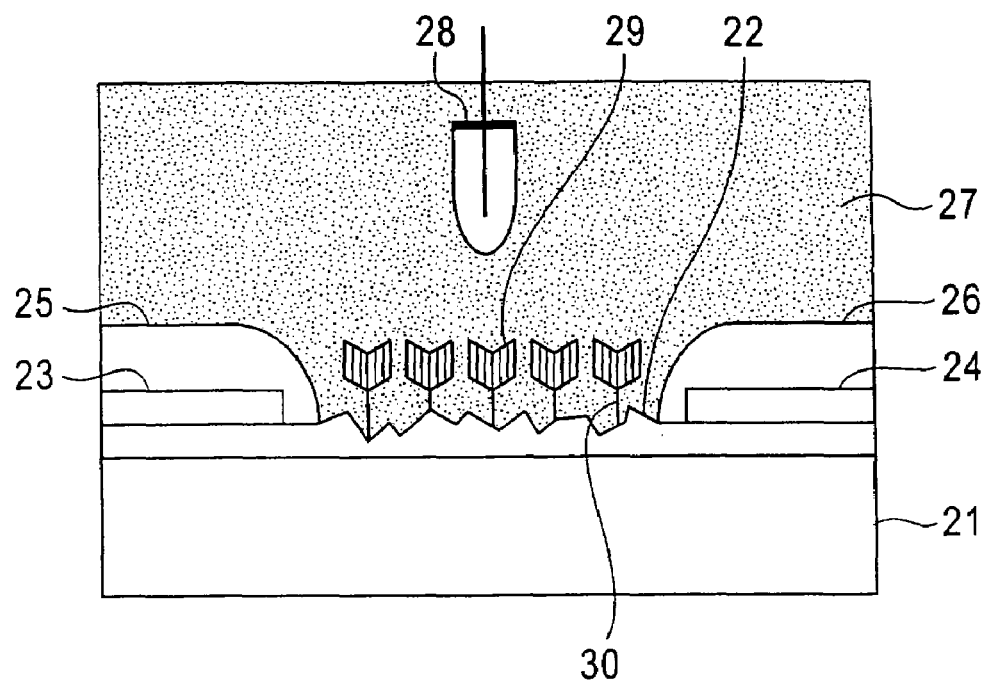
FIG. 7 is a schematic diagram of an enzyme biosensor with a solution gate, wherein urease is immobilized on an amino-terminated diamond surface, according to an embodiment of the present invention.
Figure 8:
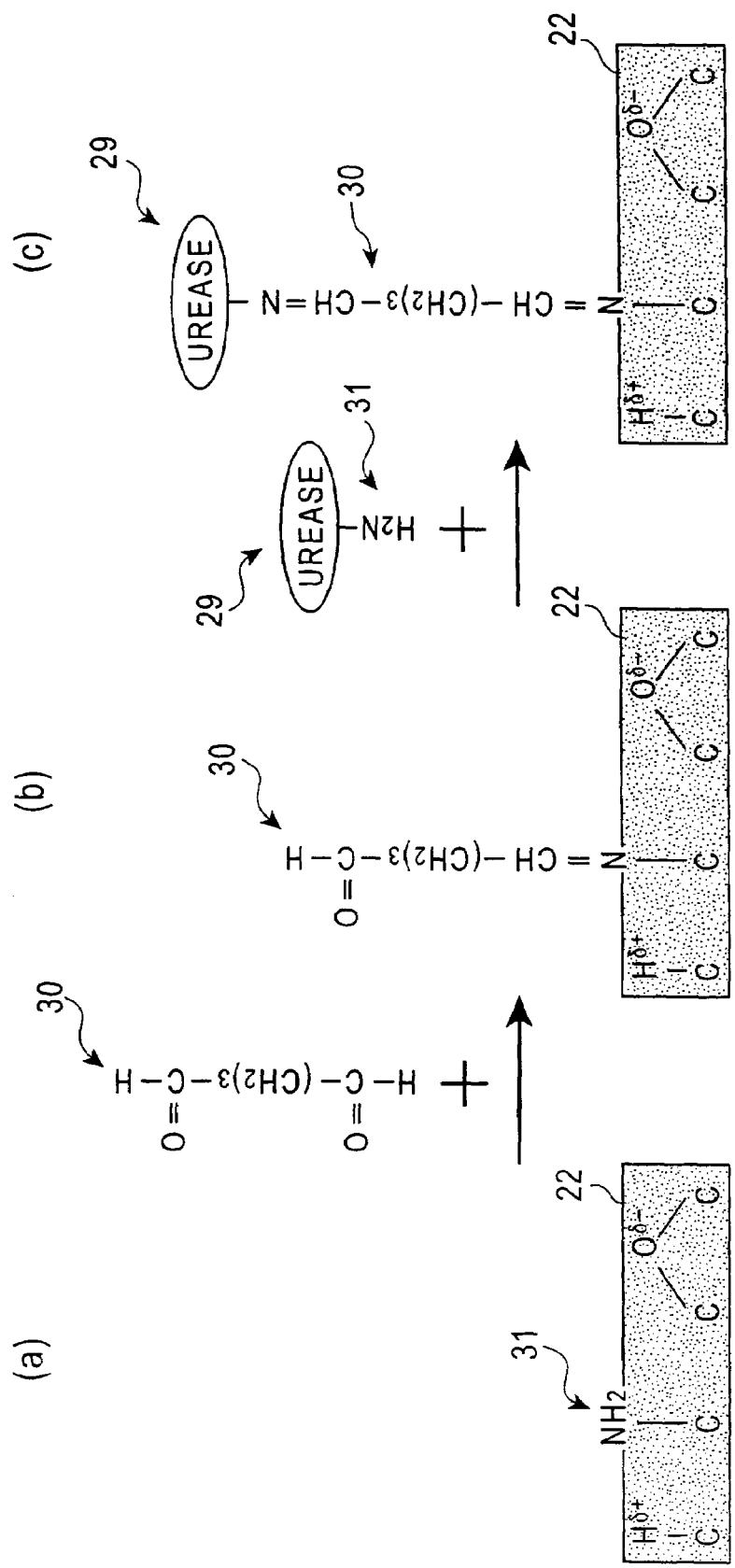
FIG. 8 is a schematic diagram showing the action of urease on an amino-terminated diamond surface according to an embodiment of the present invention.

FIG. 7 is a schematic diagram of an enzyme biosensor with a solution gate in which urease is immobilized on an amino-terminated diamond surface, according to an embodiment of the present invention. FIG. 8 is a schematic diagram showing the action on the amino-terminated diamond surface.

In these drawings, reference numeral 21 denotes a polycrystalline CVD diamond substrate, reference numeral 22 denotes a diamond surface having mixed hydrogen terminals, oxygen terminals, and amino terminals, reference numeral 23 denotes a source electrode (Au), reference numeral 24 denotes a drain electrode (Au), reference numeral 25 denotes an epoxy resin covering the source electrode (Au) 23, reference numeral 26 denotes an epoxy resin covering the drain electrode (Au) 24, reference numeral 27 denotes an urea solution, reference numeral 28 denotes a gate electrode, reference numeral 29 denotes an immobilized enzyme, reference numeral 30 denotes glutaraldehyde, and reference numeral 31 denotes an amino group.

When a diamond surface 22 having mixed hydrogen terminals, oxygen terminals, and amino terminals is treated under the action of glutaraldehyde $OHC(CH_2)_3CHO$ 30, as shown in FIG. 8(a), the glutaraldehyde 30 is immobilized to the amino group 31 on the diamond surface 22 having mixed hydrogen terminals, oxygen terminals, and amino terminals, as shown in FIG. 8(b). When urease 29 is further applied thereto, the amino group 31 of the urease 29 is bonded to the glutaraldehyde 30, as shown in FIG. 8(c). That is, the urease 29 can be immobilized on the diamond surface 22 having mixed hydrogen terminals, oxygen terminals, and amino terminals.

Figure 9:
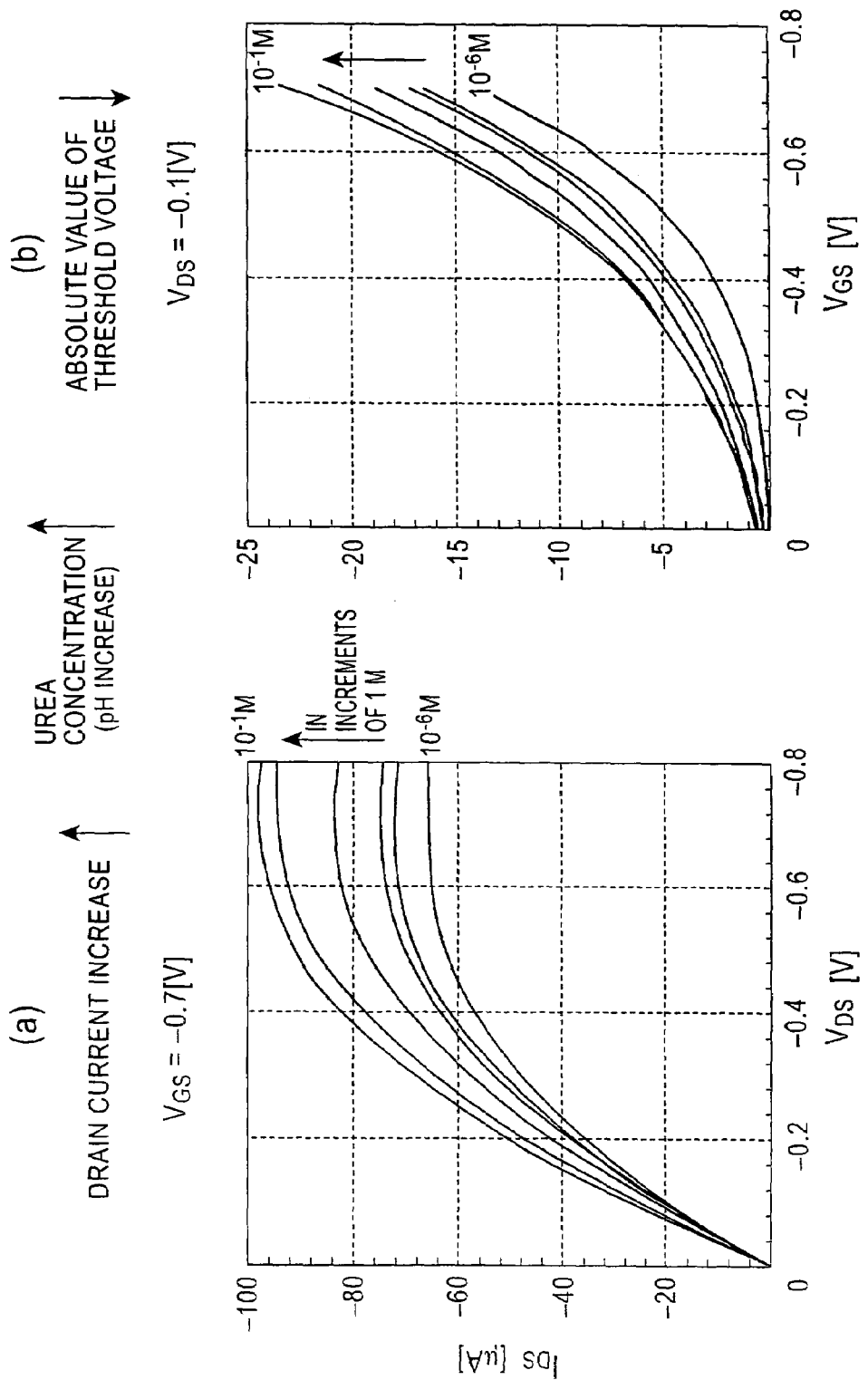
FIG. 9 is an urea concentration characteristic diagram (No. 1) of a diamond urea sensor according to an embodiment of the present invention.

FIG. 9 is an urea concentration characteristic diagram (No. 1) of a diamond urea sensor according to an embodiment of the present invention. FIG. 9(a) is a characteristic diagram showing the drain-to-source voltage. $V_{DS}$ versus the drain-to-source current $I_{DS}$ in the case where the gate-to-source voltage $V_{GS}$ is −0.7 V. FIG. 9(b) is a characteristic diagram showing the gate-to-source voltage $V_{GS}$ versus the drain-to-source current $I_{DS}$ in the case where the drain-to-source voltage $V_{DS}$ is −0.1 V.

Figure 10:
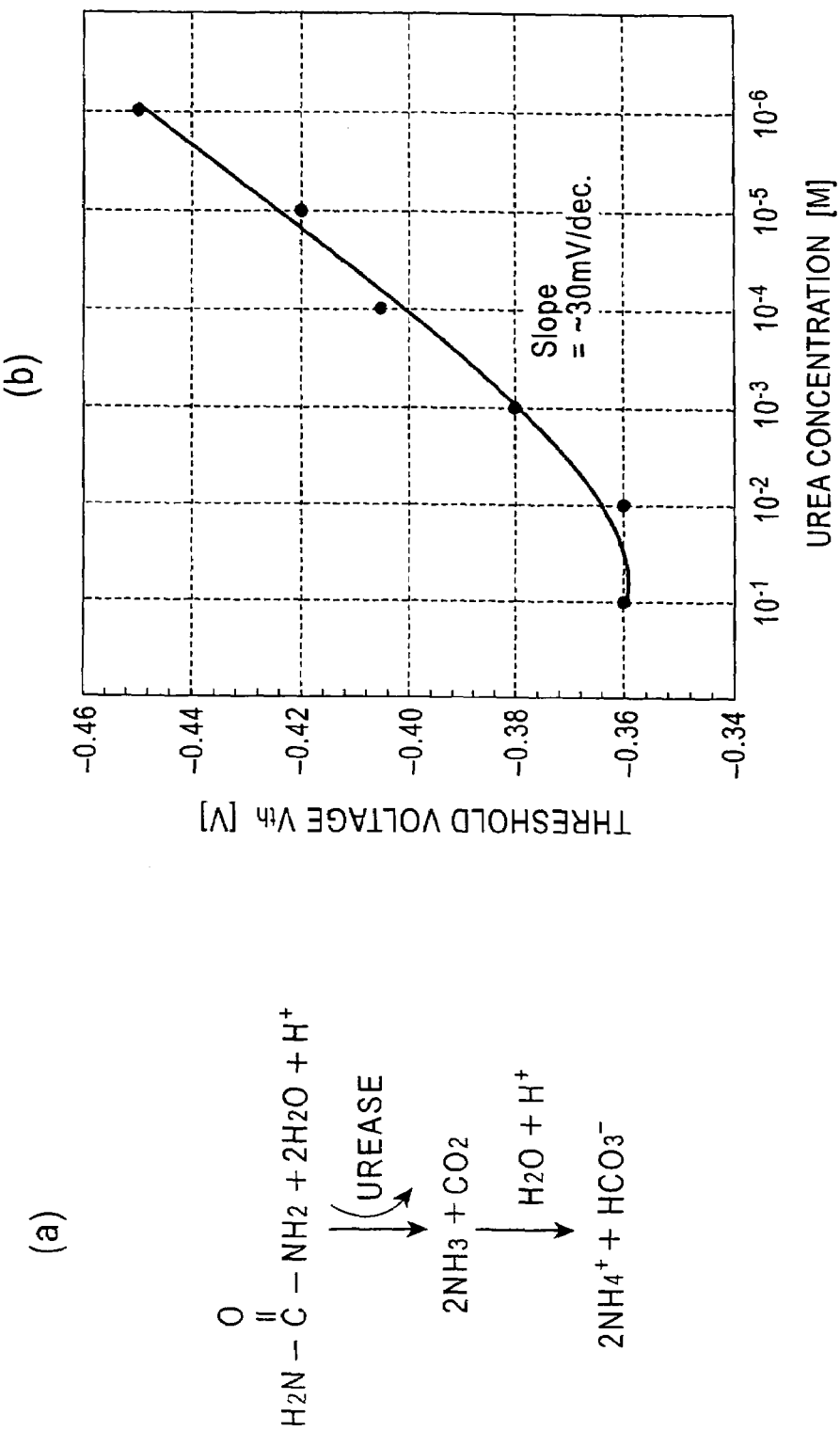
FIG. 10 is an urea concentration characteristic diagram (No. 2) of a diamond urea sensor according to an embodiment of the present invention.

FIG. 10 is an urea concentration characteristic diagram (No. 2) of a diamond urea sensor according to an embodiment of the present invention. FIG. 10(a) is an explanatory diagram of a chemical action (decomposition) of the urea. FIG. 10(b) is a sensing characteristic diagram of urea, the horizontal axis indicates the urea concentration (M), and the vertical axis indicates the threshold voltage $V_{th}$ (V).

As shown in FIG. 9, in the diamond FET with an electrolytic solution gate, where urease is immobilized, the drain current is increased and the threshold voltage shifts in the positive direction as the urea concentration is increased.

As shown in FIG. 10(a), urea is decomposed into urease in water. In the course of the decomposition, alkaline ammonia acid and acidic carbonic acid are generated. Since the alkaline ammonia acid is stronger than the acidic carbonic acid, the pH of the diamond surface is increased. The drain current of the diamond FET with an electrolytic solution gate is also increased as the pH is increased.

As described above, the diamond urea sensor of the present invention is an enzyme sensor to detect a change in pH. As shown in FIG. 10(b), the shift of the threshold voltage is about 30 mV/decade. When the urea concentration was increased from $10^{-6}$ M to $10^{-2}$ M, the threshold voltage shifted by about 0.1 V in the positive direction, and the urea concentration sensitivity of 30 mV/decade was exhibited.

The present invention is not limited to the above-described embodiments. Various modifications can be made based on the spirit of the present invention, and these are not excluded from the scope of the present invention.

As described above in detail, the following effects can be exerted according to the present invention.

(A) The sensitivity to the enzyme concentration can be enhanced by immobilizing the enzyme directly on the FET channel surface (diamond surface).

(B) A simplified measurement of the urea concentration is important in health care. In particular, it is useful for, e.g., a measurement of the urea in the blood used as an index of renal function in the clinical research.

(C) The food inspection, in particular, the inspection of urea in cow's milk can be simplified.

(D) A trace quantity of urea (μM) can be measured in a biochemical analysis.

INDUSTRIAL APPLICABILITY

The p channel field effect transistor of the present invention and a sensor including the same can be used particularly in chemical sensors and biosensors.

The invention claimed is:

1. A p channel field effect transistor used as a gate comprising:
a liquid electrolyte; and
a diamond surface that serves as a channel comprising a mixture of hydrogen terminals, oxygen terminals, and amino terminals.

2. A sensor comprising: p channel field effect transistor according to claim 1 and exhibiting a pH sensitivity through the use of a shift of threshold voltage in the positive direction on a surface having mixed amino terminals and oxygen terminals in response to an increase in pH of a liquid electrolyte.

3. The sensor according to claim 2, wherein the increase in pH is 2 to 12.

4. The sensor according to claim 3, wherein the surface supports the immobilization of an urease and a glutaldehyde, wherein the glutaldehyde is a divalent aldehyde, wherein the shift of threshold voltage occurs in the positive direction in response to an increase in urea concentration so that the increase in urea concentration is detected by the sensor.

5. The sensor according to claim 2 wherein the surface supports the immobilization of an urease and a glutaldehyde, wherein the glutaldehyde is a divalent aldehyde, wherein the shift of threshold voltage occurs in the positive direction in response to an increase in urea concentration so that the increase in urea concentration is detected by the sensor.

6. The sensor according to claim 5, wherein the increase in urea concentration is $10^{-6}$ M to $10^{-2}$ M.

7. A sensor comprising:
a diamond surface that serves as a channel comprising a mixture of hydrogen terminals and amino terminals; and
a p channel field effect transistor that serves as a gate comprising a liquid electrolyte, and that allows a shift of threshold voltage in a positive direction on the diamond surface in response to an increase in pH of the liquid electrolyte in the p channel field effect transistor so that the increase in pH is detected by the sensor.

8. The sensor according to claim 7, wherein the diamond surface supports the immobilization of an urease and a glutaldehyde, wherein the glutaldehyde is a divalent aldehyde, wherein the shift of threshold voltage occurs in the positive direction in response to an increase in urea concentration so that the increase in urea concentration is detected by the sensor.

9. The sensor according to claim 7, wherein the diamond surface is a polycrystalline diamond surface, a nanocrystalline diamond surface, or a monocrystalline diamond surface.

* * * * *